United States Patent [19]

Lemahieu et al.

[11] 4,008,085
[45] Feb. 15, 1977

[54] PHOTOSENSITIVE MATERIAL CONTAINING AN ORGANIC POLYHALOGEN COMPOUND AND A DYE PRECURSOR AND THE USE THEREOF

[75] Inventors: Raymond Gerard Lemahieu, Mortsel; Urbain Leopold Laridon, Wilrijk, both of Belgium

[73] Assignee: AGFA-GEVAERT N.V., Mortsel, Belgium

[22] Filed: Dec. 18, 1974

[21] Appl. No.: 533,890

[30] Foreign Application Priority Data

Dec. 19, 1973 United Kingdom ............. 58782/73

[52] U.S. Cl. .............................. 96/48 R; 96/48 QP;
96/45.2; 96/90 R; 96/119PQ
[51] Int. Cl.² ...................... G03C 5/24; G03C 1/52
[58] Field of Search ...................... 96/48 R, 96/45.2, 90 R, 48 QP, 119 PQ

[56] References Cited

UNITED STATES PATENTS

| 3,042,515 | 7/1962 | Wainer | 96/90 R |
|---|---|---|---|
| 3,102,029 | 8/1963 | Fichter et al. | 96/90 R |

*Primary Examiner*—Won H. Louie, Jr.
*Attorney, Agent, or Firm*—William J. Daniel

[57] ABSTRACT

A photosensitive recording material that is capable of producing directly a visible image as a result of an image-wise exposure to activating electromagnetic radiation and which contains an intimate mixture comprising:
1. at least one ultra-violet radiation-sensitive organic polyhalogen compound, and
2. a dye precursor compound corresponding to the following general formula:

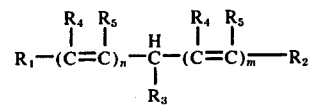

wherein:

$R_1$ represents (1) a substituted aryl group, at least one substituent of the substituted aryl group being an ether group $R_6$—O— in which $R_6$ represents a hydrocarbon group, including a substituted hydrocarbon group or (2) a heterocyclic group including a substituted heterocyclic group, $R_2$ represents a substituted aryl group, at least one substituent of the substituted aryl group, being an ether group $R_6$—O—, in which $R_6$ represents a hydrocarbon group, including a substituted hydrocarbon group, a heterocyclic group including a substituted heterocyclic group, or a

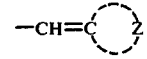

group in which Z represents the necessary atoms to close a heterocyclic nucleus including a substituted heterocyclic nucleus, $R_3$ represents (1) a —XH or —X—$R_7$ group, in which X is oxygen and $R_7$ is an organic group, (2) a

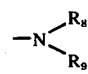

group wherein each of $R_8$ and $R_9$ (same or different) represents hydrogen or an alkyl group, a cycloalkyl group, an aralkyl group, or an aryl group or $R_8$ and $R_9$ together represent the necessary atoms to close a nitrogen-containing heterocyclic nucleus, each of $R_4$ and $R_5$ (same or different) represents hydrogen, a $C_1$-$C_5$ alkyl group, a cycloalkyl group, an aralkyl group or an aryl group, $n$ is 0 or 1, and $m$ is 0 or 1.

19 Claims, No Drawings

PHOTOSENSITIVE MATERIAL CONTAINING AN ORGANIC POLYHALOGEN COMPOUND AND A DYE PRECURSOR AND THE USE THEREOF

This invention relates to photographic recording and reproduction of information and to materials suited therefor.

Free radical photography has been described already by R. A. Fotland in J. Phot. Sci., Vol. 18 (1970) 33-37.

By the term "free radical photosensitive material" employed in the present description is meant a photosensitive material in which at least one of the photosensitive ingredients is an ultraviolet sensitive organic polyhalogen compound producing photoradicals on exposure with said radiation. The free radicals are of the type that form an acid by reaction with an hydrogen donator. The image-wise produced acid is used to form a dye with a dye precursor compound.

Photographic dye-forming systems based on the use of said polyhalogen compound and an acid sensitive dye precursor compound have been described e.g. in the U.S. Pat. Nos. 3,042,515 and 3,102,029.

In all these dye-forming systems carbon tetrabromide and/or iodoform are the most commonly used photoradicalgenerating compounds because these compounds excel in photosensitivity when compared with other representatives of the class of photosensitive organic polyhalogen compounds.

A photographic recording process has been found in which methine dye salts of various colours are formed by photographically producing an acid-reacting compound that is allowed to react with a dye precursor compound corresponding to the following general formula:

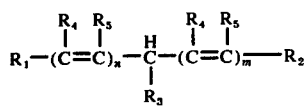

wherein:

$R_1$ represents (1) a substituted aryl group e.g. a substituted phenyl, tolyl, xylyl, naphthyl, biphenyl, or indenyl group at least one substituent of said aryl group being an ether group $R_6$—O— in which $R_6$ represents a hydrocarbon group including a substituted hydrocarbon group, e.g. an alkyl group including a substituted alkyl group, e.g. a methyl, ethyl, propyl, hexyl, dodecyl, or octadecyl group, a cycloalkyl group including a substituted cycloalkyl group e.g. a cyclopentyl, cyclohexyl, or methylcyclohexyl group, an aralkyl group including a substituted aralkyl group e.g. a benzyl or phenethyl group, an aryl group including a substituted aryl group e.g. a phenyl group or tolyl group or (2) a heterocyclic group including a substituted heterocyclic group e.g. an indolyl, pyrryl, thienyl, furyl, carbazolyl or indolizinyl group, the thienyl group being preferably substituted with a N-morpholinyl group, $R_2$ represents a substituted aryl group e.g. a substituted phenyl, tolyl, xylyl, naphthyl, biphenyl or indenyl group, at least one substituent of said groups being an ether group $R_6$—O—, in which $R_6$ represents a hydrocarbon group including a substituted hydrocarbon group, e.g. an alkyl group including a substituted alkyl group, e.g. a methyl, ethyl, propyl, hexyl, dodecyl, or octadecyl group, a cycloalkyl group including a substituted cycloalkyl group e.g. a cyclopentyl, cyclohexyl, or methylcyclohexyl group, an aralkyl group including a substituted aralkyl group e.g. a benzyl or phenethyl group, an aryl group including a substituted aryl group e.g. a phenyl group or tolyl group or a heterocyclic group including a substituted heterocyclic group e.g. an indolyl, pyrryl, thienyl, furyl, carbazolyl, or indolizinyl group, the thienyl group being preferably substituted with a N-morpholinyl group, or a

group in which Z represents the necessary atoms to close a heterocyclic nucleus including a substituted heterocyclic nucleus e.g. a nitrogen-containing heterocyclic nucleus, the indolylidene-(2) group being an example thereof, $R_3$ represents (1) a —XH or —X—$R_7$ group in which X is oxygen and $R_7$ is an organic group e.g. an alkyl group including a substituted alkyl group e.g. methyl, a cycloalkyl group including a substituted cycloalkyl group e.g. a cyclohexyl group, an aralkyl group including a substituted aralkyl group e.g. a benzyl group, an aryl group including a substituted aryl group e.g. a phenyl group, or an heterocyclic group including a substituted heterocyclic group, (2) a

group wherein each of $R_8$ and $R_9$ (same or different) represents hydrogen or an alkyl group e.g. a $C_1$—$C_5$ alkyl group, a cycloalkyl group, an aralkyl group, or an aryl group or $R_8$ and $R_9$ together represent the necessary atoms to close a nitrogen-containing heterocyclic nucleus e.g. a piperidine, pyrrolidine, or morpholine nucleus, each of $R_4$ and $R_5$ (same or different) represents hydrogen, a $C_1$—$C_5$ alkyl group, a cycloalkyl group, an aralkyl group e.g. benzyl or an aryl group e.g. a phenyl group, $n$ is 0 or 1, and $m$ is 0 or 1.

The dye precursor compounds involved do not contain acid substituents.

Representatives of particularly suitable dye precursor compounds are given in the following table 1.

Table 1

| No. | Dye precursor compound | Colour of dye | Melting point °C |
|---|---|---|---|
| 1 | (structure) | blue-green | 120 |
| 2 | (structure) | blue-green | 70 |
| 3 | (structure) | blue | 115 |
| 4 | (structure) | blue | 165 |
| 5 | (structure) | green | 177 |

Table 1-continued

| No. | Dye precursor compound | Colour of dye | Melting point °C |
|---|---|---|---|
| 6 | | magenta | 204 |
| 7 | | brown | 160 |
| 8 | | magenta | 175 |
| 9 | | blue | 270 |
| 10 | | yellow | 150 |
| 11 | | brown red | 234 |

The preparation of the dye precursor compounds is illustrated by the following detailed preparation receipts.

1. Preparation of dye precursor compound 1

12.24 g (0.06 mole) of 3-phenyl-propiolic aldehyde dissolved in 50 ml of ethanol were added dropwise to 25 g (0.12 mole) of 1-methyl-2-phenylindole dissolved in a mixture of 75 ml of ethanol and 25 ml of ethanol saturated with hydrogen chloride gas. The reaction mixture was cooled down to 0° C, whereupon the dyestuff crystallized.

Yield: 24.2 g. Melting point: 235° C.

6 g of dyestuff were dissolved in 100 ml of methylene chloride and allowed to react with 6 ml of piperidine. The solvent was evaporated and the residue washed with water and methanol.

2. Preparation of dye precursor compound 6

9.8 g (0.05 mole) of 2,4,6-trimethoxybenzaldehyde were added portion-wise to a solution of 10.35 g (0.05 mole) of 1-methyl-2-phenylindole in a mixture of 75 ml of ethanol and 75 ml of ethanol saturated with hydrogen chloride. During the addition of the benzaldehyde derivative the reaction mixture was stirred and kept at 15° C by cooling.

After a reaction period of 2 hours a solution of 12.5 g of sodium perchlorate in 50 ml of methanol was added. The crystallized dyestuff was separated and recrystallized from ethanol.

Yield: 11 g. Melting point: 204° C.

To 5 g of the dyestuff dissolved in 50 ml of methylene chloride 2.5 ml of morpholine were added. After washing with water and drying with potassium carbonate the solvent was evaporated. Yield: 4.3 g. Melting point: 204° C.

3. Preparation of dye precursor compound 7

At 15° C 500 ml of ethanol saturated with hydrogen chloride gas were added dropwise to a solution of 168 g (1 mole) of 1,3,5-trimethoxybenzene and of 90 g (0.55 mole) of malondialdehyde tetramethylacetal in 500 ml of dry ethanol. The dyestuff corresponding to the dye precursor compound crystallized in the reaction mixture. After separation the dyestuff was first washed with a mixture of ethanol and ether (1:9 by volume) and subsequently with ether alone.

1300 ml of a 10% by weight aqueous sodium carbonate solution were added with stirring to 120 g of the dyestuff dissolved in a mixture of 1000 ml of methylene chloride and 200 ml of methanol. The reaction mixture became colourless and the obtained dye precursor compound dissolved in the organic liquid phase. The leuco base was crystallized from acetonitrile. Yield: 59.7 g. Melting point: 160° C.

4. Preparation of dye precursor compound 8

84 ml of concentrated sulphuric acid were added dropwise to 500 ml of methanol while cooling the mixture 124 g (0.36 mole) of 2-morpholino-3,4-diphenylthiophene were added to the mixture obtained. 80.4 g of N-ethyl-3-formylcarbazole dissolved in 750 ml of ethanol were added dropwise with thorough stirring to the solution obtained at a temperature between 10° and 15° C over a period of 2 hours. The reaction mixture was kept at room temperature for a further 2 hours, thereupon cooled down, whereafter the crystals obtained were sucked off. The resulting precipitate was washed three times with 400 ml of water.

Yield of dyestuff: 194 g. Melting point: 236° C.

150 g of the obtained dyestuff were dispersed into a mixture of 500 ml of methylene chloride and of 50 ml of methanol. Then 250 g of aqueous ammonia were added to the mixture with cooling. The organic phase was separated and dried with anhydrous potassium carbonate. The solvent was evaporated and the residue digested in benzine.

Yield of the leuco base: 130 g. Melting point: 175° C.

5. Preparation of dye precursor compound 10

At 10° C 375 ml of ethanol saturated with hydrogen chloride were added dropwise to a solution of 42 g (0.25 mole) of 1,3,5-trimethoxybenzene and 49 g (0.25 mole) of 2,4,6-trimethoxybenzaldehyde. The dyestuff that crystallized in the reaction mixture was sucked off and washed first with a small amount of cold ethanol and afterwards with ether.

Yield: 55.2 g. Melting point approximately 140° C.

45.2 g of the obtained dyestuff were dissolved in a mixture of 450 ml of methylene chloride and of 45 ml of methanol and converted into the colourless leuco form by mixing it with a 675 ml of a 10% by weight aqueous solution of sodium carbonate. The leuco base passed into the organic phase. The solvent was evaporated. The residue left contained the leuco base.

Yield: 26 g. Melting point: 150° C.

The aromatic and heterocyclic aldehydes used in the above described preparations have been prepared by the Vilsmeyer reaction which reaction has been described e.g. by Donald J. Cram and George S. Hammond in "Organic Synthesis"— 2nd Edition (1964) McGraw-Hill Book Company Ind. New York — p. 446–447 and by Houben-Weyl in Methoden der Organische Chemie Vol.III, part 1, p. 30.

As an example of the synthesis of said aldehydes the following preparation is given in detail:

Preparation of 1-methyl-2-phenyl-3-formyl-indole

To 150 ml of dimethylformamide 46 ml of phosphorus oxychloride were added dropwise care being taken that the temperature of the reaction mixture did not rise above 20° C. Subsequently to the obtained mixture 103.5 g of 1-methyl-2-phenyl-indole dissolved in 200 ml of dimethylformamide were added dropwise. During the addition the temperature of the reaction mixture was kept in the range of 20° to 40° C and thereupon for 1 hour between 40° and 45° C. Then the reaction mixture was poured into a solution of 490 g of sodium acetate dissolved in 500 ml of water to which 500 g of ice were added. The precipitated aldehyde was separated by suction, washed with water and methanol.

Yield: 105 g. Melting point: 125° C.

Starting products such as 2,5-dimethylpyrrole derivatives have been prepared analogously to the synthesis of 2,5-dimethyl-pyrrole described in Org. Synth. Coll. Vol. II, 219.

The synthesis of 2-morpholino-3,4-diphenyl-thiophene has been described by H. Hartmann and R. Mayer, Z. Chem. 6, 28 (1966).

The synthesis of the indole derivatives has been carried out analogously to the synthesis of 2-phenyl-indole as described by W. E. Noland et al., J. Org. Chem. 31, 65–69 (1966).

The synthesis of 2,3-diphenylindolizine has been carried out analogously to the synthesis of substituted indolizines described e.g. in the United Kingdom Patents Nos. 658,560 filed April 1, 1949 and 999,874 filed July 21, 1960 both by Kodak Ltd.

The above dye precursors yield dyes with a particularly high dye stability, in other words dyes that particularly well withstand fading by prolonged daylight exposure. Due to the large variety of chemical substituents a large spectrum of highly saturated colours is obtainable.

The dye precursors themselves are very stable so that the shelf life of the present recording materials in the absence of light is very well.

Suitable organic polyhalogen compounds, from which a halogen-containing radical can be separated photolytically, are within the scope of the following general formula:

wherein:
each of A, B, X and Y is a halogen atom of the group of chlorine, bromine or iodine, or wherein one of said groups A, B, X or Y represents an alkyl group, including a substituted alkyl group e.g. a halogen-substituted alkyl group, a hydroxy-alkyl group or an aralkyl group e.g. benzyl, an aryl group, a substituted aryl group or an aroyl group and the other groups chlorine, bromine, or iodine.

Particularly suitable representatives falling within the scope of that general formula are organic halides such as carbon tetrabromide, bromoform, iodoform, hexachloroethane, hexabromoethane, pentabromoethane, 1,1,2,2-tetrabromoethane, α,α,α-tribromoacetophenone and tribromoethanol.

Without any limit of the scope of the present invention it is assumed that the colour-forming reaction takes place along the following reaction scheme:

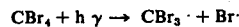 (1)

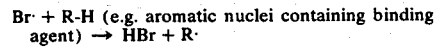 (2)

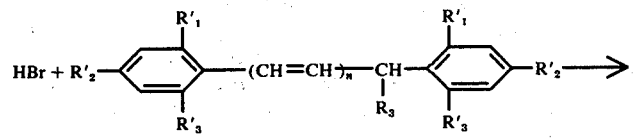 (3)

a methine dye probably having a resonance system of the following type:

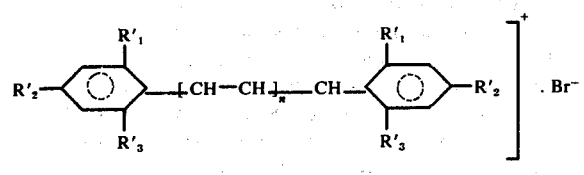

wherein:
$R_3$ has the definition described above e.g. is a —OH or —OCH$_3$ group,
$R'_1$, $R'_2$, and $R'_3$ are methoxy groups, and
$n$ is 0, 1 or 2.

According to a preferred embodiment the recording materials of the present invention contain a dye precursor compound or mixture of dye precursor compounds in intimate admixture with said photosensitive polyhalogen compound in a binder medium in layer form applied to a support.

Particularly suitable binders for that purpose are hydrophobic polymers and copolymers, e.g. containing styrene, vinyl acetate, acrylonitrile, acrylic acid ester, methacrylic acid ester or butadiene units, hydrophobic cellulose derivatives, phenoxy resins or polycondensates of the polyester type, e.g. polycarbonates and binding agents increasing the sensitivity such as polymers containing N-vinylcarbazole units.

The polymers serving as binding agent can be used in a mixture for improvement of the mechanical strength or adhesion power of the recording layer to its support, when no self-supporting layer is produced.

In order to diminish the rate of spontaneous thermal colour formation over long periods of time as might be encountered during storage of the photographic material and processing of the photographic materials, so-called anti-foggants may be added to the photosensitive composition. Suitable anti-foggants include sterically hindered phenols, e.g. 2,6-di-tert.butyl-p-cresol and a triaryl compound of a group V element e.g. triarylstibine as described e.g. in the United Kingdom Patent Application No. 44,200/73.

Preferred photosensitive recording materials according to the present invention contain the dye precursor compound(s) and photosensitive polyhalogen compound in a ratio by weight within the range of 10:100 to 200:100.

Preferred amounts of anti-fogging agent such as triphenylstibine with respect to photosensitive carbon tetrabromide and/or iodoform are within the weight ratio range of 1:100 to 2.5:100.

A dry photographic coating containing the above mentioned ingredients can be formed by dissolving the binding agent(s) in a suitable inert solvent, which acts as dispersing or dissolving medium for the other ingredients, and by removing the solvent from the coating composition by evaporation so that a solid photographic recording layer is left on a properly chosen support. The supports may be of any kind encountered in silver halide photographic materials, e.g. opaque paper and transparent film supports, e.g. subbed and unsubbed polyethylene terephthalate ester supports.

The recording materials of the present invention containing the colour-forming compounds of the general formula in combination with polymers and copolymers that contain N-vinylcarbazole units and that serve as binding agent show a remarkable high sensitivity to U.V. radiation. This high sensitivity is still increased when during the U.V. exposure the temperature of the recording layer composition is raised above 40° C. A very suitable operating temperature is in the range of 40°–70° C.

The recording materials according to the present invention are suited to produce print-out images of different colour according to the particular colour forming compound applied. In a particular preferred composition for forming print-out prints a mixture of carbon tetrabromide and iodoform is used, which yields a superadditive sensitivity effect.

The stabilisation of the obtained prints may proceed by washing out the residual free radical generator with a suitable solvent or solvent mixture, e.g. a hydrocarbon liquid such as petroleum ether optionally mixed with acetone, or by simply evaporating it by raising the temperature when the compound involved is sufficiently volatile. For the latter purpose and the high photosensitivity, carbon tetrabromide or a mixture of carbon tetrabromide and iodoform is preferred. A useful stabilisation temperature is in the range of 100° to 160° C. During the heat stabilisation an increase of the image density is obtained. Preferred stabilisation techniques are described in the United Kingdom Patent Applications Nos. 32,149/72 and 44,200/73.

According to a preferred recording and reproduction process of the present invention the information-wise exposure is carried out in such a way that first a latent image is produced, which subsequently is transformed into a visible dye image by means of a so-called "optical development".

The optical development proceeds by overall exposing the recording layer containing the latent or barely visible image with visible radiation that lies in the spectral absorption band of the coloured products formed by the image-wise exposure and image-wise interaction of the photosensitive polyhalogen compound and dye precursor compound of the mentioned photosensitive composition. In the overall exposure no light is applied to which the photosensitive polyhalogen compound is inherently sensitive since this would effect an overall colouration. It is advantageous to use in the optical development exposure a filter absorbing all the light corresponding with the wavelength range that is inherently absorbed by the ingredients of the non-previously exposed recording layer.

The optical development effect is markedly speeded up and the image density increased by applying heat, e.g. supplied by contact with a hot body or through infrared radiation during the overall exposure to visible light.

The optical development speed obtains a high value by the use of poly-N-vinylcarbazole or the copolymers containing N-vinylcarbazole units in combination with the present colour forming compounds.

It is assumed that during the exposure applied in the optical development at least a part of the overall applied light energy is visible light absorbed by a dyestuff salt having the methine dye salt structure. Said salt seems to act as a spectral sensitizing agent for a chemical reaction between the photosensitive polyhalogen compound or radicals formed therefrom and the dye precursor compound.

According to an alternative embodiment of the optical development technique the recording material is first overall exposed to electromagnetic radiation in order to produce non-differentially over the whole recording layer latent dyestuff centres that afterwards are optically developed information-wise by a sufficiently strong information-wise exposure in the absorption band of the dyestuff centres. Optionally the information-wise exposure proceeds simultaneously with an overall heating, effected e.g., by an overall infrared exposure.

The information-wise exposure applied in the present invention may be a contact exposure of the direct of reflex type and likewise an optical projection exposure as is used, e.g., in an optical enlarging apparatus. The information-wise exposure need not be simultaneous in all parts of the recording material. The exposure may be progressive in one continuous step as, e.g., in sound track recording, or in successive intermittent steps provided that the required information-wise change is obtained. Thus the recording material may be scanned with an image-wise modulated radiant energy spot of high intensity e.g. a laser beam, or the material may be progressively exposed through a slit, e.g. to copying light of a tubular lamp that is given a translation movement along the original.

A recording material of the present invention being suited for the recording of information in the form of modulated ultraviolet radiation can be used in X-ray and laser beam recording. X-ray beams can be absorbed in substances absorbing high energy and by means of them create so-called secundary photons, e.g. of the ultraviolet radiation energy band, and photoelectrons that are absorbed by the photosensitive polyhalogen compound forming through its photoradicals a dyestuff salt with the colour forming compound. Substances for high energy absorption that may be incorporated into the recording element contain the elements lead, mercury, bismuth, barium and/or tungsten. Lead compounds that are photosensitive by themselves are preferred, e.g. lead monoxide, lead bromide and lead iodide.

Suitable light sources for use in a recording method of the present invention are ultra-violet radiation sources, xenon-gas lamps, incandescent bulbs and flash lamps. Sunlight is also suited in the overall exposure. For the optical development an infra-red lamp emitting also in the visible spectrum is preferably used.

Laser beam recording proceeds with the apparatus suited for that purpose and known to those skilled in the art.

Recording materials of the present invention are very versatile in that they can be applied for continuous tone or halftone reproduction. They can offer very contrasty images so that they are very suited for the reproduction of line and screen type originals and find a successful use in a great variety of graphic art applications. Due to the very high resolving power of the recording materials (the dyestuffs are formed in molecularly divided form) the recording materials of the present invention are particularly suited for microfilm reproduction and high precision image rendering as e.g. in the production of optical micromask masters used in the manufacturing of microelectronic circuitry.

According to a special application a recording layer as described herein is used in conjunction with a magnetic recording layer and is more particularly applied to the rear side of a flexible tape support carrying the magnetic recording layer. On such a material a sound track is formed in the magnetic recording layer and a visual text image corresponding with the sound track is photographed on the recording layer of the present invention. Such a recording material thus allows the storing of optical and acoustic signals and makes it possible to reproduce both informations simultaneously.

The present invention is illustrated by the following examples. The percentages and ratios are by weight unless otherwise indicated.

EXAMPLE 1

A mixture of 100 mg of carbon tetrabromide, 100 mg of iodoform, 100 mg of a colour forming compound indicated by number in Table 1 and 20 mg of triphenylstibine was dissolved in 10 ml of a 5% poly-N-vinylcarbazole solution in methylene chloride.

The solution was coated at a thickness of 0.10 mm onto a non-subbed polyethylene terephthalate support and dried at 50° C in the dark at room temperature.

Print-out processing

The recording material was exposed for 2 min through a step wedge of constant 0.15 by means of a 80 W high pressure mercury vapour lamp type HPL of Phillips' Gloeilampenfabrieken — Eindhoven (Netherlands) placed at a distance of 10 cm.

The obtained images were stabilized by means of a 2 min heat treatment at 180° C.

The obtained results expressed by the number of reproduced wedge steps are listed in the following table 2.

Table 2

| Number of the colour forming compound | Amount of reproduced steps |
| --- | --- |
| 1 | 9 |
| 2 | 11 |
| 3 | 12 |
| 4 | 11 |
| 5 | 8 |
| 6 | 9 |
| 7 | 9 |
| 8 | 8 |
| 9 | 12 |
| 10 | 9 |
| 11 | 10 |

EXAMPLE 2

A mixture of 100 mg of iodoform, 100 mg of a colour forming compound indicated by number in the Table 1 and 100 mg of 2,6-di-t.butyl-p-cresol was dissolved in a 10% solution of EPONOL-RESIN 55-B-40 (trade name for an epoxy resin of SHELL Cy.) in 50 volume parts of methylene chloride, 35 volume parts of trichloroethylene and 15 volume parts of butanone.

The solution was coated at a thickness of 0.10 mm onto a non-subbed polyethylene terephthalate support and dried in the dark at 50° C.

The recording layer was exposed for 2 min through a step wedge of constant 0.15 by means of 80 W high pressure mercury vapor lamp type HPL of Philips placed at a distance of 10 cm.

The obtained images were stabilized by means of a 2 min heat treatment at 150° C.

The obtained results expressed by the number of reproduced wedge steps are listed in the following table 3.

Table 3

| Number of the colour forming compound | Amount of reproduced steps |
| --- | --- |
| 1 | 11 |
| 3 | 8 |
| 4 | 10 |

EXAMPLE 3

A recording material as described in Example 1 containing dye precursor 4 for the print-out processing was used in optical development processing.

In the optical development processing the recording material was image-wise exposed with the same ultraviolet light source as applied in the print-out exposure but the exposure lasted now only 2 sec.

The optical development was carried out by overall exposing the image-wise exposed recording material with a 250 W infrared lamp type 13372 of N. V. Philips' Gloeilampenfabrieken Eindhoven, Netherlands, emitting also in the visible spectrum and placed at a distance of 15 cm. The overall exposure time for reaching a maximum density (blue image) $(d_{max})$ equal to 0.7 was 45 sec. During the overall exposure a cut-off filter was used absorbing all the light having a wavelength smaller than 540 nm.

EXAMPLE 4

The following intimately mixed composition was coated at wet coating thickness of 0.10 mm to an unsubbed polyethylene terephthalate support:

| | |
| --- | --- |
| carbon tetrabromide | 100 mg |
| iodoform | 100 mg |
| dye precursor compound 3 | 100 mg |
| 10 % solution of EPONOL-RESIN 55-B-40 (trade name) in a 2:1 mixture by volume of $CH_2Cl_2$ and butanone | 10 ml |

The exposure of the dried material was carried out through a transparent line original for 2 sec with the ultraviolet lamp of Example 1 placed at a distance of 10 cm.

The optical development was carried out by overall exposing the image-wise exposed recording material with the 250 W infra-red lamp of Example 3 placed at a distance of 15 cm. The infra-red exposure lasted 30 sec.

During the infra-red exposure a cut-off filter was used absorbing all the light having a wavelength smaller than 540 nm.

A blue dye image of strong density was obtained. The image was stabilized by heating the recording material for 2 min at 180° C.

What we claim is:

1. A photographic process wherein a visible image is formed in a recording material, which contains in intimate admixture an image-forming system consisting essentially of:
    1. at least one ultra-violet radiation-sensitive organic polyhalogen compound corresponding to the following general formula:

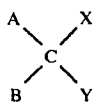

wherein:
each of A, B, X and Y are halogen atoms of the group of chlorine, bromine, or iodine, or
wherein one of said groups A, B, X or Y represents an alkyl group, an aryl group or an aroyl group and the other groups chlorine, bromine, or iodine, and
2. a dye precursor compound corresponding to the following general formula:

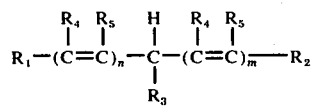

wherein:
$R_1$ represents (1) a substituted aryl group, at least one substituent of the substituted aryl group being an ether group $R_6$—O— in which $R_6$ represents a hydrocarbon group, or (2) a heterocyclic group containing a 5 - membered nitrogen - containing heterocyclic nucleus,
$R_2$ represents (1) a substituted aryl group, at least one substituent of the substituted aryl group, being an ether group $R_6$—O—, in which $R_6$ represents a hydrocarbon group, (2) a heterocyclic group containing a 5 - membered nitrogen - containing heterocyclic nucleus, or (3) a

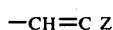

group in which Z represents the necessary atoms to close a 5-membered nitrogen containing heterocyclic nucleus, $R_3$ represents (1) a —XH or —X—$R_7$ group, in which X is oxygen and $R_7$ is an alkyl group, or (2) a

group wherein each of $R_8$ and $R_9$ (same or different) represents hydrogen or an alkyl group, a cycloalkyl group, an aralkyl group, or an aryl group or $R_8$ and $R_9$ together represent the necessary atoms to close a 5- or 6-membered nitrogen-containing heterocyclic nucleus,
each of $R_4$ and $R_5$ (same or different) represents hydrogen, a $C_1$—$C_5$ alkyl group, a cycloalkyl group, an aralkyl group or an aryl group,
$n$ is 0 or 1, and
$m$ is 0,
said visible image being formed (A) by the step of:
information-wise exposing the recording material to activating electromagnetic radiation of a dose sufficient to bring about a directly visible image, or (B) by the steps of:
information-wise exposing the recording material to activating electromagnetic radiation of a dose sufficient to bring about a latent or barely visible image, the image portions of which have a spectral sensitivity in a wavelength range outside the inherent sensitivity range of the ultraviolet radiation-sensitive polyhalogen compound, and overall exposing the image-wise exposed recording material to light within the wavelength range for which the initially exposed portions are made more sensitive than the initially non-exposed portions, thereby bringing about the formation of a visible image corresponding with the initially information-wise exposed portions, or (C) by the steps of:
overall exposing the recording material to electromagnetic radiation of a dose sufficient to bring about in the recording material an increase in spectral sensitivity in a wavelength range outside the inherent sensitivity range of the ultra-violet radiation-sensitive polyhalogen compound, and information-wise exposing the thus overall exposed recording material within the wavelength range for which the overall exposed portions of the recording material are made more sensitive.

2. A photographic process according to claim 1, wherein the recording material after the formation of a visible image is overall heated to bring about image stabilisation.

3. A photographic process according to claim 1, wherein $R_1$ and/or $R_2$ represent a methoxy substituted phenyl group.

4. A photographic process according to claim 1, wherein $R_1$ and/or $R_2$ (same or different) represent an indolyl, pyrryl, thienyl, furyl carbazolyl or indolizinyl group including such groups in substituted form.

5. A photographic process according to claim 1, wherein $R_3$ represents a N-piperidinyl or N-morpholinyl group.

6. A process according to claim 1, wherein said ultraviolet radiation-sensitive compound is carbon tetrabromide or iodoform.

7. A process according to claim 1, wherein in the recording material a mixture of carbon tetrabromide and iodoform is used.

8. A process according to claim 1, wherein in the recording material in combination with said mixture as anti-fogging agent a triaryl compound of a group V element and/or a sterically hindered phenol is used.

9. A process according to claim 1, wherein the mixture is used in one or more binding agents, selected from the group of polymers and copolymers comprising styrene, vinyl acetate, acrylonitrile, acrylic acid ester, methacrylic acid ester, N-vinylcarbazole or butadiene units, a hydrophobic cellulose derivative, a phenoxy resin or a polycondensate of the polyester type including a polycarbonate resin.

10. A process according to claim 1, wherein the exposure is a direct exposure.

11. A photosensitive recording material that is capable of producing directly a visible image as a result of an image-wise exposure to activating electromagnetic radiation and which contains in intimate admixture an image-forming system consisting essentially of:
1. at least one ultra-violet radiation-sensitive organic polyhalogen compound corresponding to the following general formula:

wherein:
each of A, B, X, and Y are halogen atoms of the group of chlorine, bromine, or iodine, or
wherein one of said groups A, B, X or Y represents an alkyl group, an aryl group or an aroyl group and the other groups chlorine, bromine, or iodine, and 2. a dye precursor compound corresponding to the following general formula:

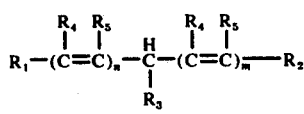

wherein:
$R_1$ represents (1) a substituted aryl group, at least one substituent of the substituted aryl group being an ether group $R_6$—O— in which $R_6$ represents a hydrocarbon group or (2) a heterocyclic group containing a 5-membered nitrogen-containing heterocyclic nucleus, $R_2$ represents (1) a substituted aryl group, at least one substituent of the substituted aryl group, being an ether group $R_6$—O—, in which $R_6$ represents a hydrocarbon group, (2) a heterocyclic group containing a 5 - membered nitrogen - containing heterocyclic nucleus or (3) a

—CH=C Z group in which Z represents the necessary atoms to close a 5-membered nitrogen-containing heterocyclic nucleus, $R_3$ represents (1) a —XH or —X—$R_7$ group, in which X is oxygen and $R_7$ is an alkyl group, (2) a

group wherein each of $R_8$ and $R_9$ (same or different) represents hydrogen or an alkyl group, a cycloalkyl group, an aralkyl group, or an aryl group or $R_8$ and $R_9$ together represent the necessary atoms to close a 5- or 6-membered nitrogen-containing heterocyclic nucleus, each of $R_4$ and $R_5$ (same or different) represents hydrogen, a $C_1$—$C_5$ alkyl group, a cycloalkyl group, an aralkyl group or an aryl group, $n$ is 0 or 1, and $m$ is 0.

12. A photosensitive recording material according to claim 11, wherein $R_1$ and/or $R_2$ represent a methoxy-substituted phenyl group.

13. A photosensitive recording material according to claim 11, wherein $R_1$ and/or $R_2$ (same or different) represent an indolyl, a pyrryl, a thienyl, a furyl, a carbazolyl or an indolizinyl group.

14. A photosensitive recording material according to claim 11, wherein $R_3$ is a N-piperidinyl group or a N-morpholinyl group.

15. A photosensitive recording material according to claim 11, wherein said ultraviolet radiation-sensitive compound is carbon tetrabromide or iodoform.

16. A photosensitive recording material according to claim 11, wherein the recording material contains a mixture of carbon tetrabromide and iodoform.

17. A photosensitive recording material according to claim 11, wherein the mixture is present in a binder layer.

18. A photosensitive recording material according to claim 17, wherein said material contains in a layer said mixture and poly-N-vinylcarbazole or a copolymer containing N-vinyl carbazole units as sole binding agent.

19. A photosensitive recording material according to claim 11, containing as antifogging agent a triaryl compound of a group V element and/or a sterically hindered phenol.

* * * * *

UNITED STATES PATENT AND TRADEMARK OFFICE
CERTIFICATE OF CORRECTION

PATENT NO. : 4,008,085
DATED : February 15, 1977
INVENTOR(S) : Raymond Gerard Lemahieu et al It is certified that error appears in the above-identified patent and that said Letters Patent are hereby corrected as shown below:

In the Claims:

Column 15, the formula between lines 35 and 40 should read -- $-CH=C\begin{pmatrix}Z\end{pmatrix}$ --.

Column 17, the formula between lines 35 and 40 should read -- $-CH=C\begin{pmatrix}Z\end{pmatrix}$ --.

Signed and Sealed this

Twenty-sixth Day of April 1977

[SEAL]

Attest:

RUTH C. MASON
*Attesting Officer*

C. MARSHALL DANN
*Commissioner of Patents and Trademarks*